United States Patent [19]
Witt

[11] Patent Number: 5,007,902
[45] Date of Patent: Apr. 16, 1991

[54] CATHETER SET FOR PLEXUS ANESTHESIA

[75] Inventor: Hans-Hinrich Witt, Koerle, Fed. Rep. of Germany

[73] Assignee: B. Braun Melsungen AG, Melsungen, Fed. Rep. of Germany

[21] Appl. No.: 313,706

[22] Filed: Feb. 22, 1989

[30] Foreign Application Priority Data

Mar. 9, 1988 [DE] Fed. Rep. of Germany ... 8803153[U]

[51] Int. Cl.$^5$ ............................................. A61M 5/162
[52] U.S. Cl. ................................... 604/117; 604/164; 604/170; 128/741
[58] Field of Search ............... 128/642, 741, 784, 786; 604/117, 164, 170

[56] References Cited

U.S. PATENT DOCUMENTS

| 3,406,685 | 10/1968 | May ............................ 604/170 X |
| 4,685,904 | 8/1987 | Krebs ............................ 604/164 |
| 4,824,433 | 4/1989 | Marz et al. ........................ 128/741 X |

FOREIGN PATENT DOCUMENTS

| 0158397 | 10/1985 | European Pat. Off. ............ 128/741 |
| 3014892 | 10/1980 | Fed. Rep. of Germany ...... 128/784 |
| 8222222 | 11/1982 | Fed. Rep. of Germany . |

Primary Examiner—Lee S. Cohen
Attorney, Agent, or Firm—Spensley Horn Jubas & Lubitz

[57] ABSTRACT

The invention provides a catheter set for plexus anesthesia wherein the catheter can be displaced under electric stimulation and the position of the catheter can be checked also afterwards. The catheter set is provided with a puncture cannula, a capillary plugged onto said puncture cannula, and a catheter which can be inserted through said capillary and has an open patient-side end. Into the catheter, a guide wire can be inserted, being provided with an electric contact means at its end distant from the patient and having its patient-side end exposed. The position of the guide wire and the catheter end, respectively, in the fascia can be checked by electric pulses. When the catheter remains set for a longer time period, subsequent insertion of the guide wire makes it possible to monitor and, if need be, correct the position of the catheter at all times.

5 Claims, 1 Drawing Sheet

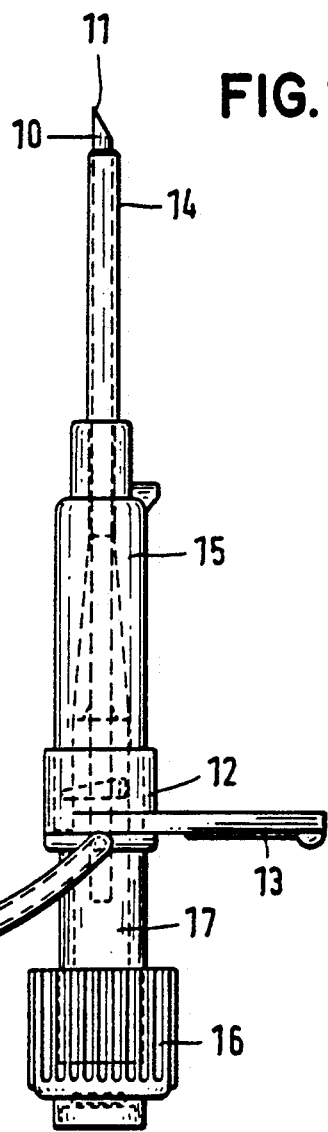
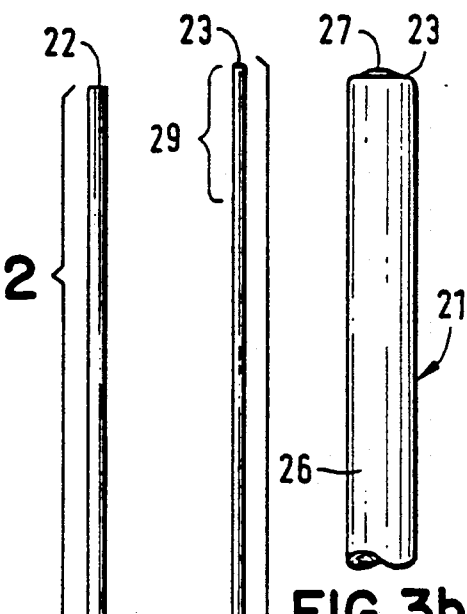
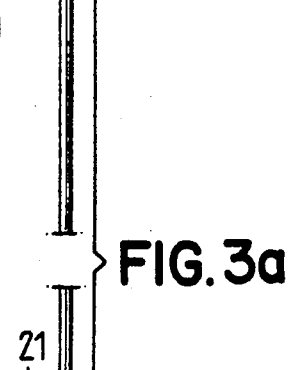
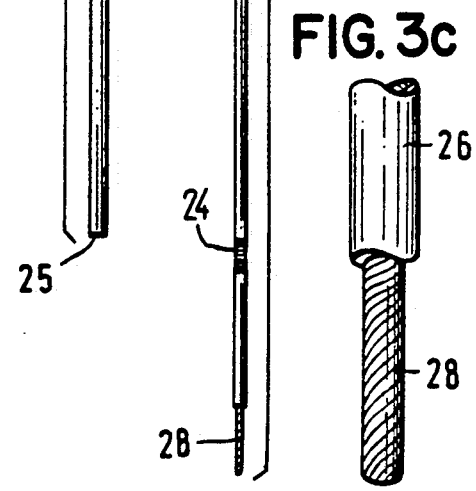

CATHETER SET FOR PLEXUS ANESTHESIA

BACKGROUND OF THE INVENTION

1. Field of the Invention

The invention is directed to a catheter set for plexus anesthesia.

2. Description of Related Art

In a catheter set as known from German Utility Model 82 22 222, a plastic capillary is plugged onto a puncture cannula having its front end provided with a suitable bevel. After puncture of the nerve vessel, the puncture cannula is drawn out of the capillary, and a catheter is inserted into the capillary, through which catheter an anesthetic can be administered to the patient.

Disadvantageously, the known plexus catheter requires much experience and skill and makes it very difficult to locate the nerve undergoing treatment. Besides, the capillary and/or the catheter may kink, which hinders advance of the catheter.

There is also known a catheter set for plexus anesthesia wherein there is used a mandrel coated with plastic material in order to increase stiffness when setting the catheter. This stiffness of the mandrel, in particular, can cause injuries to fine nerve branches. Moreover, precise control of the catheter position is not possible using this catheter set.

It is an object of the present invention to provide a catheter set wherein the catheter can be introduced under electric stimulation and the catheter position can also be checked afterwards.

SUMMARY OF THE INVENTION

In accordance with the present invention, this and other objectives are achieved by providing a guide wire to be inserted into the catheter. The guide wire exerts a stiffening effect on the catheter and facilitates setting thereof. The guide wire also serves as an electric conduit for neurostimulation.

The front end of the guide wire, protruding slightly out of the catheter, is exposed. A contact means is arranged at the rear end of the guide wire. Thus, the respective position of the guide wire and the catheter end in the fascia can be checked by electric pulses. If the catheter remains in use for an extended time period, later insertion of the guide wire allows monitoring the position of the catheter at all times and, if necessary, correcting the position of the catheter.

A marking, provided on the guide wire, indicates when only the tip of the guide wire protrudes out of the insulating catheter. In this manner, the patient-side ends of the plexus catheter and the guide wire can be adjusted relative to each other. The exposed front end of the guide wire is not enclosed by the catheter, so that the exposed end contacts the tissue. By stimulating the nerves with the guide wire, the correct position of the catheter can be checked whenever necessary, even after days or weeks.

BRIEF DESCRIPTION OF THE DRAWINGS

A detailed description of a preferred embodiment of the invention will be made with reference to the accompanying drawings, wherein like numerals designate corresponding parts in the several figures.

FIG. 1 shows a preferred embodiment of the puncture cannula with a capillary plugged on.

FIG. 2 shows a preferred embodiment of the catheter with a guide wire.

FIG. 3, in an enlarged scale, shows the two end sections of a guide wire.

DESCRIPTION OF THE PREFERRED EMBODIMENTS

The following detailed description is of the best presently contemplated mode of carrying out the invention. This description is not to be taken in a limiting sense, but is made merely for the purpose of illustrating the general principles of the invention. The scope of the invention is best defined by the appended claims.

In the embodiment of the invention illustrated in FIG. 1, the catheter set is provided with a steel puncture cannula 10 having a special bevel 11 at its front end. The bevel 11 allows penetrating the fascia wall without destroying the nerve fibers. At the rear end of the cannula 10, there is arranged a cannula hub 12 comprising a handle 13. The capillary 14, preferably consisting of a plastic material, is pushed onto the cannula 10 and is used as an insertion means for the catheter 20. The front end of the capillary 14 is arranged at a small distance behind the bevel 11. At the rear end of the capillary 14, there is provided a hub member 15, preferably consisting of plastic material. The hub member 15 engages with the cannula hub 12 and can be locked by a Luer locking device. At the rear end of the cannula hub 12, a connecting member 17, closed by a stopper 16, is provided for connecting a syringe to the cannula 10 during punctuation of the nerve-vessel separating wall.

The metallic cannula 10 is electrically connected to a plug 19 through a cable 18, the plug 19 being adapted for connection to a nerve stimulator (not shown).

In the embodiment shown in FIG. 1, the puncture cannula 10 may be used for locating the nerve in the fascia cover by electrical stimulation. For this purpose, electric pulses are applied to the puncture cannula 10. If the end of the puncture cannula 10, protruding out of the capillary 14, maintains a position in the immediate vicinity of the respective nerve; e.g., at a distance of less than one to two mm, an irritation is effected in the nerve, causing a reflex movement of the respective member (e.g., a finger).

After removal of the puncture cannula 10, the capillary 14 may remain in the body of the patient to enable insertion of the catheter 20. The catheter 20 is shifted onto the guide wire 21 and, in this condition, is introduced into the fascia through the capillary 14. Thus, the respective front ends 22 and 23 of the catheter 20 and the guide wire 21 are generally flush, but the guide-wire end 23 slightly protrudes out of the catheter end 22. This condition is detected by the guide wire 21 having its rear portion provided with a color marking 24. The color marking 24 reaches the rear end 25 of the catheter 20 when the front ends 22 and 23 maintain the correct mutual position.

In the preferred embodiment, the guide wire 21 is provided with an electrically insulating layer 26 extending over its entire length, leaving free only the front blank wire-end 27 and a noninsulated portion 28 at the rear end, which noninsulated portion forms the contact means. Different markings, distributed over the length of the catheter 20, may be arranged on the catheter for detecting the depth of penetration of the catheter with respect to the hub 15.

The guide wire 21 may serve for exact detection of the position of the front end 22 of the catheter 20 by neuro-stimulation. For this purpose, a neurostimulator may be connected to the contact means 28. Electric pulses, issuing from the blank wire end 27, act on the surrounding tissue. In this manner neurostimulation is performed through the guide wire 21 and thus detection of the position of catheter opening 22 with regard to the nerve plexus. The guide wire 21 also acts as a stiffening element for the catheter 20. The front end portion 29 of the guide wire 21 is preferably softer than the rest of the length thereof, so as to preclude damage to sensitive fine nerve-branches.

After the catheter 20 has been placed, the guide wire 21 can be drawn out of the catheter.

Checking the position of the catheter 20 is possible at all times by inserting a new guide wire 21 into the catheter. In this manner, the position of the catheter 20 can be checked by neurostimulation through the guide wire 21. If necessary, the position of the catheter 20 can be changed by displacing the catheter and the guide wire 21.

The catheter 20 preferably has the typical small thickness of plexus catheters, with an outer diameter preferably of about 1.05 mm and an inner lumen preferably of 0.65 mm. The diameter of the corresponding guide wire 21 is preferably about 0.6 mm, so that the guide wire fills the catheter lumen but can be displaced within the catheter without considerable friction.

The presently disclosed embodiments are therefore to be considered in all respects as illustrative and not restrictive, the scope of the invention being indicated by the appended claims, rather than the foregoing description, and all changes which come within the meaning and range of equivalency of the claims are therefore intended to be embraced therein.

What is claimed is:

1. A catheter set for plexus anesthesia, comprising:
a puncture cannula,
a capillary releasably fastened to the puncture cannula,
a catheter adapted for insertion through the capillary, the catheter having a front end and a rear end, the front end of the catheter being open,
an electrically conductive guide wire adapted for insertion into the catheter, the guide wire having a front end and a rear end,
means for indicating the relative position of the guide wire and the catheter, and
an electric contact provided at the rear end of the guide wire, the electric contact being adapted for electrical connection to a neurostimulator,
wherein the position of the catheter in the fascia can be determined by neurostimulation through the guide wire.

2. The catheter set according to claim 1, wherein the guide means for indicating the relative position of the guide wire and the catheter comprises a marking provided substantially adjacent the rear end of the guide wire for indicating the depth of insertion of the guide wire into the catheter.

3. The catheter set according to claim 1, wherein the cannula is electrically conductive and further comprising an electrically conductive connection element connected to the puncture cannula, the connection element being adapted for electrical connection to a neurostimulator.

4. A catheter set for plexus anesthesia, comprising:
a puncture cannula,
a capillary releasable fastened to the puncture cannula,
a catheter adapted for insertion through the capillary, the catheter having a rear end and a front end, the front end of the catheter being open,
an electrically conductive guide wire adapted for insertion into the catheter, the guide wire having a rear end and a front end, and
an electric contact provided at the rear end of the guide wire, wherein at least a portion of the front end of the guide wire is relatively softer than the remaining length of the guide wire.

5. A catheter set for plexus anesthesia, comprising:
a puncture cannula,
a capillary releasably fastened to the puncture cannula,
a catheter adapted for insertion through the capillary, the catheter having a rear end and a front end, the front end of the catheter being open,
an electrically conductive guide wire adapted for insertion into the catheter, the guide wire having a rear end and a front end, and
an electric contact provided at the rear end of the guide wire, and
an insulating coating provided on the guide wire, the insulating coating leaving exposed the front end and the rear end of the guide wire.

* * * * *